(12) United States Patent
Su et al.

(10) Patent No.: US 6,784,226 B2
(45) Date of Patent: Aug. 31, 2004

(54) PROCESS FOR PRODUCING A STYRENIC RESIN COMPOSITION

(75) Inventors: Wen-Yi Su, Tainan (TW); Perry Dong-Bi Shiueh, Tainan (TW)

(73) Assignee: Chi Mei Corporation, Tainan Hsien (TW)

( * ) Notice: Subject to any disclaimer, the term of this patent is extended or adjusted under 35 U.S.C. 154(b) by 162 days.

(21) Appl. No.: 10/247,941

(22) Filed: Sep. 20, 2002

(65) Prior Publication Data

US 2003/0114559 A1 Jun. 19, 2003

Related U.S. Application Data

(63) Continuation-in-part of application No. 09/363,284, filed on Jul. 28, 1999, now abandoned.

(51) Int. Cl.[7] .............................. C08K 9/04; C08K 9/06
(52) U.S. Cl. ....................... 523/205; 523/209; 523/210; 523/216
(58) Field of Search ........................ 523/205, 209–210, 523/216

(56) References Cited

U.S. PATENT DOCUMENTS

| | | | |
|---|---|---|---|
| 3,240,751 A | 3/1966 | Cannon et al. | 524/151 |
| 3,382,199 A | 5/1968 | Scullin | 524/157 |
| 3,654,178 A | 4/1972 | Kauder et al. | 252/400.24 |
| 4,000,100 A | 12/1976 | Baldyga | 252/400.24 |
| 4,138,363 A | 2/1979 | Hertzenberg et al. | 252/455 |
| 4,154,718 A | 5/1979 | Miyata et al. | 524/436 |
| 4,443,572 A | 4/1984 | Burns | 524/120 |
| 4,540,727 A | 9/1985 | Vogdes | 524/83 |
| 4,810,579 A | 3/1989 | Neri et al. | 428/405 |
| 4,820,772 A | 4/1989 | Goto et al. | 524/141 |
| 4,857,230 A | 8/1989 | Matsumura | 524/400.24 |
| 4,923,918 A | 5/1990 | Komori et al. | 524/351 |
| 5,001,176 A | 3/1991 | Nakazima | 524/108 |
| 5,010,123 A | 4/1991 | Worschech et al. | 524/114 |
| 5,141,995 A | 8/1992 | Komori et al. | 525/242 |
| 5,208,362 A | 5/1993 | Glass et al. | 558/146 |
| 5,252,633 A | 10/1993 | Ohara et al. | 524/451 |
| 5,326,803 A | 7/1994 | Avarian et al. | 524/120 |
| 5,338,777 A | 8/1994 | Tarquini | 524/450 |
| 5,416,141 A | 5/1995 | Endres et al. | 524/109 |
| 5,846,656 A | 12/1998 | Dunski | 524/400.24 |
| 5,856,550 A | 1/1999 | Linhart et al. | 558/71 |
| 6,005,034 A | 12/1999 | Hagashida et al. | 524/141 |
| 6,013,706 A | 1/2000 | Kleiner et al. | 524/126 |

FOREIGN PATENT DOCUMENTS

| | | |
|---|---|---|
| JP | 5937021 | 9/1984 |
| JP | 62167346 | 7/1987 |
| JP | 7278164 | 10/1995 |

OTHER PUBLICATIONS

Patent Abstracts of Japan Publication No. 07–278164 Dated Oct. 24, 1995.
Patent Abstracts of Japan Publication No. 62–167346 Dated Jul. 23, 1987.

*Primary Examiner*—Peter Szekely
(74) *Attorney, Agent, or Firm*—Ladas & Parry (57) ABSTRACT

A process for producing a styrenic resin composition includes the step of compounding a styrenic resin with greater than 2 wt % water and an antioxidant which is prepared by blending (a) 20 to 99.9 wt % of organic phosphite or phosphonite with (b) 0.1 to 80 wt % of acid-binding metal salt treated with a surface conditioning agent, prior to compounding with the styrenic resin.

8 Claims, 1 Drawing Sheet

FIG. 1

PROCESS FOR PRODUCING A STYRENIC RESIN COMPOSITION

CROSS-REFERENCE TO RELATED APPLICATION

This application is a continuation-in-part application Ser. No. 09/363,284 filed on Jul. 28, 1999, now abandoned which designated the U.S., claims the benefit thereof and incorporates the same by reference.

BACKGROUND OF THE INVENTION

1. Field of the Invention

This invention relates to a process for producing a styrenic resin composition, more particularly to a process for preparing a styrenic resin composition that contains a styrenic resin and an organic phosphorus-containing antioxidant.

2. Description of the Related Art

Styrenic resins, such as acrylonitrile-butadiene styrene copolymeric resin (ABS resin), can be used for the production of automobile parts, electronic parts and office automation appliances, due to their high impact strength, good stiffness, and excellent characteristic for molding and processing.

ABS resin is usually prepared by compounding styrene-acrylonitrile copolymer prepared by solution polymerization techniques and dry powdery acrylonitrile-butadiene-styrene grafted copolymer prepared by emulsion polymerization techniques with lubricants and stabilizers, such as phosphorous-containing antioxidant (e.g. Tris nonyl phenyl phosphite) via in an extruder at a temperature of 180° C. or higher. Usually, preparation of the dry powdery acrylonitrile-butadiene-styrene graft copolymer having a water content of less than 1 wt % involves the steps of coagulation and dewatering of the ABS graft copolymer latex to get the wet powdery acrylonitrile-butadiene-styrene grafted copolymer having a water content ranging from 15 to 40 wt % and followed by drying of the wet powdery graft copolymer with hot air. The process is complicated and uneconomical. Moreover, there is also a high risk of fire during the drying of the wet powder. The thus-formed acrylonitrile-butadiene-styrene graft copolymer powder having been dried with hot air tends to result in yellowish in appearance and poor thermal stability.

Japanese Publication No. 59-37021 discloses a method for producing ABS resin by extruding the aforesaid coagulated and dewatered wet powdery acrylonitrile-butadiene-styrene graft copolymer and styrene-acrylonitrile copolymer in an extruder that includes a silt type dewatering section and vent ports. Though the method dispenses with the aforesaid drying step, high extrusion temperature (above 200° C.) and high water content of the wet powder results in high moisture content in the extruder, which, in turn, results in hydrolysis of the phosphorous-containing antioxidant blended therewith, thereby resulting in poor thermal stability of the ABS resin. Furthermore, tris nonyl phenyl phosphite is one of the commonly used phosphorous-containing antioxidants for ABS resin, and it can be hydrolyzed to form nonyl phenol which has been shown to have an effect to interfere endocrine of human body and animal body and thus is harmful to the environment. Therefore, for a long time of the ABS industry, it is necessary to overcome the drawback of poor stability to hydrolysis of the phosphorous-containing antioxidants during processing of ABS resin, especially at a high temperature and a high humidity condition during extrusion as encountered in the aforesaid method.

Phosphorous-containing antioxidants tend to hydrolyze very easily at a high temperature and high moisture condition. Such hydrolysis generates phosphoric acid, thereby further expediting the rate of the hydrolysis. As such, the hydrolysis not only decreases the antioxidative property of the composition, but also causes damages to equipment, and brings about undesirable pollution. Accordingly, there is a long need in this industry to avoid hydrolysis of phosphorous containing antioxidant during the production of ABS resin. In order to solve the disadvantages described above, it is normally proposed to add organic amines in the reaction to decrease the rate of the hydrolysis of the phosphorus-containing antioxidant. Examples of the amines described above are hexamethylene tetramine, triisopropanoyl amine, stearyl dimethyl amine, and the like. However, the improvement is not satisfied, and the presence of the amine will affect the chemical property of the resin and generate poison as well. Therefore, the amine is inappropriate for use. Moreover, organic amines are normally used along with liquid phosphide antioxidant, such as tri-nonyl-phenyl phosphite, di-phenyl isodecyl phosphite, di-phenyl-isooctyl phosphite, tri-phenyl phosphite, 4,4'-iso-propylidene-diphenol-alkyl (C12–15) phosphite, and the like.

Another method for stabilizing against hydrolysis is to enhance the sterical hindrance of the substitutent (such as phenolic group) at the ortho-position phenolic to hinder water from contacting the phosphorus, thereby effectively preventing the occurrence of hydrolysis. One such example is an antioxidant Irgafos 168 (a trade name, available from Ciba geigy Chemicals Corporation) which is tris(di-tert-butyl-2,4-phenyl) phosphite and which consists of three phenolic groups substituted at the ortho-position with tertiary butyl substitutents and which has the following formula (I):

(I)

While hydrolysis of the antioxidant of formula (I) can be reduced, however, the composition also reduces the affinity of the phosphorus for oxygen, thereby weakening the antioxidative property. As such, more phosphorus containing antioxidant has to be added in order to achieve the same property.

To improve the disadvantage described above, U.S. Pat. No. 5,856,550 proposed another method for stabilizing against hydrolysis by adding inorganic acid-binding agent into the phosphorus-containing antioxidant in combination with the amines to achieve the purpose for stabilizing against hydrolysis. Examples of the inorganic acid-binding agent are metal oxide, metal carbonate, metal carboxylate, hydrotalcite, zeolite, and the like. By using the inorganic acid-binding agent in combination with triisopropanyl amine to absorb the phosphoric acid generated from the hydrolysis of the phosphorus-containing antioxidant, the rate of the hydrolysis in an acid condition can be deterred. However, since the affinity of the inorganic acid binding agent for the organic phosphorus compounds is weak, poor stabilization of the phosphorus-containing antioxidant results when the agent is non-uniformly distributed. Moreover, the addition of organic amines will result in problems, such as initial color of the resin, thermal stability during processing, and generation of toxic gas.

U.S. Pat. Nos. 4,810,579 and 5,326,803 disclose the use of reactive coupling agent for encapsulating the surface of the organic phosphorus compounds, thereby utilizing the hydrophobic characteristic of the coupling agent for water to achieve the purpose of stabilizing against hydrolysis. While the methods described above may be useful for powdered organic phosphorus compounds stored in a high atmospheric humidity, they are still insufficient to effectively stabilize against hydrolysis when they are subjected to a high humidity condition with a temperature above 200° C. For example, in case of blending the organic phosphorus compounds with the resin, followed by extruding from an extruder at a high humidity and a high temperature (above 100° C.), the stability to hydrolysis cannot be achieved with the above described methods.

U.S. Pat. No. 4,820,772 discloses a composition obtained by blending high density ethylene polymer and non-crystalline ethylene-propylene random polymer. Additives, such as organic phosphite compounds and zeolite can be added into the composition. The zeolite used can be silane treated.

U.S. Pat. No. 4,923,918 discloses a method for producing a modified propylene polymer. The method involves blending a mixture of propylene polymer, phenolic antioxidant, radical generator, and zinc salt of a carboxylic acid. Additives, such as recite zeolite (which can be silane treated) and organic phosphites, can be added into the propylene polymer.

U.S. Pat. No. 5,001,176 discloses a crystalline polyolefin composition that contains crystalline polyolefin, dibenzylidenesorbital type compound, and cyclodextrin. Additives, such as zeolites, silane coupling agents and organic phosphites, can be added into the polyolefin.

U.S. Pat. No. 5,141,995 discloses a modified propylene polymer prepared by blending propylene polymer with polyol or partial ester of polyol, phenolic antioxidant, and radical generating agent. Additives, such as recite zeolite, and organic phosphites can be added into the polymer.

U.S. Pat. No. 6,005,034 discloses a method for producing propylene-ethylene copolymer. Additives, such as zeolite, silane coupling agent and organic phosphites, can be added into dried propylene-ethylene copolymer.

Unlike the aforesaid wet powdery acrylonitrile-butadiene-styrene graft copolymer for the preparation of ABS resin, the raw materials (ethylene polymer, propylene polymer, ethylene-propylene copolymer) used in the aforementioned patents are free of water and have no adverse effect on the organic phosphites. Therefore, these patents fail to teach how the aforesaid hydrolysis problem can be solved via the use of zeolite treated with silane and organic phosphites during extrusion at a high humidity and a high temperature condition. Moreover, organic phosphites, zeolite and the polymers employed in these patents are added into a mixer or an extruder, respectively. Therefore, none of these patents teaches mixing of organic phosphites and zeolite prior to mixing or compounding with the polymers in order to enhance stability of organic phosphites against hydrolysis.

U.S. Pat. No. 4,138,363 discloses a hydrophilic silane-zeolite composition and a method for producing the same. The composition is formed by condensing a hydrophilic silane onto the surface of a hydrated zeolite. The patent fails to teach neither the application of the composition to styrenic resin nor the stability of hydrolysis of phosphorus-containing anti-oxidant processed at a high temperature and a high humidity condition.

SUMMARY OF THE INVENTION

Therefore, it is proposed to overcome the problems described above by modifying the composition of the organic phosphorus containing antioxidant so as to render the same to exhibit good stability to hydrolysis when it is subjected to a high temperature and a high humidity condition.

Therefore, it is an object of this invention to provide an organic phosphorus-containing antioxidant which exhibits good stability to hydrolysis, and which results in good initial color of the resin composition, and which enhances thermal stability during processing and eliminates the generation of toxic gas.

It is another object of this invention to provide an organic phosphorus-containing antioxidant which is capable of enhancing the processability and stability to hydrolysis of resins which are blended with the former, and which can further comprise a carrier and then added directly to the resins.

Thus, this invention is characterized by an organic phosphorus-containing antioxidant comprising: an organic phosphite or organic phosphonite; and an acid-binding metal salt treated with a surface conditioning agent. A carrier can be further included as needed to form an antioxidant which exhibits excellent stability to hydrolysis and antioxidative property when it is subjected to a high temperature and a high atmospheric humidity condition. The above described antioxidant can be used as additives for polymers.

It is a further object of this invention to provide a process for producing a styrenic resin composition comprising the steps of compounding 100 parts by weight of a styrenic resin having a water content greater than 2% by weight, and 0.01 5.0 parts by weight of an organic phosphorus-containing antioxidant in an extruder to form the styrenic resin composition. The phosphorous-containing antioxidant is formed by mixing (a) 20 to 99.9 wt % of organic phosphite or phosphonite with (b) 0.1 to 80 wt % of acid-binding metal salt treated with a surface conditioning agent, prior to mixing or compounding with the styrenic resin. The weight ratio of the surface conditioning agent to the acid-binding metal salt is 0.1 to 50 wt %:99.9 to 50 wt %. The surface conditioning agent is selected from the group consisting of silane coupling agents, titanate coupling agents, zirconate coupling agents, aluminate coupling agents, zirco-aluminate coupling agents, non-ionic surfactants, and anionic surfactants. The styrenic resin having a water content greater than 2% by weight comprises 5–100 wt % of a rubbery graft copolymer (A) and 95–0 wt % of a styrenic copolymer(B), based on the total weight of the styrenic resin (dry base). The rubbery graft copolymer(A) is prepared by graft polymerization of 50–90 wt % of styrenic monomer, 10–50 wt % of vinyl cyanide monomer, and 0–10 wt % of copolymerizable monomer in the presence of a rubbery polymer latex, followed by coagulation and recovery to have a water content of 5–50 wt %. The styrenic copolymer(B) is prepared by coploymerization of 50–90 wt % of styrenic monomer, 10–50 wt % of vinyl cyanide monomer, and 0 40 wt % of copolymerizable monomer.

DETAILED DESCRIPTION OF THE PREFERRED EMBODIMENTS

The process for preparing the styrenic resin composition of this invention includes the step of compounding 100 parts by weight of a styrenic resin having a water content greater than 2% by weight, and 0.01–5.0 parts by weight of an organic phosphorus containing antioxidant in an extruder to form the styrenic resin composition. The phosphorous-containing antioxidant is formed by mixing (a) 20 to 99.9 wt % of organic phosphite or phosphonite with (b) 0.1 to 80 wt % of acid-binding metal salt treated with a surface conditioning agent, prior to mixing or compounding with the styrenic resin. The weight ratio of the surface conditioning agent to the acid-binding metal salt is 0.1 to 50 wt %:99.9 to 50 wt %. The surface conditioning agent is selected from the group consisting of silane coupling agents, titanate coupling agents, zirconate coupling agents, aluminate coupling agents, zirco-aluminate coupling agents, non-ionic surfactants, and anionic surfactants. The styrenic resin having a water content greater than 2% by weight contains 5–100 wt % of rubbery graft copolymer(A) and 95–0 wt % of styrenic copolymer(B). The rubbery graft copolymer(A) is prepared by graft polymerization of 50 90 wt % of styrenic monomer, 10–50 wt % of vinyl cyanide monomer, and 0–40 wt % of copolymerizable monomer in the presence of rubbery polymer latex, followed by coagulation and recovery to have a water content of 5–50 wt %. The styrenic copolymer(B) is prepared by copolymerization of 50–90 wt % of styrenic monomer, 10 50 wt % of vinyl cyanide monomer, and 0–40 wt % of copolymerizable monomer.

The phosphite of this invention is represented by the formula P(OR)$_3$, wherein the substitutents R represent hydrocarbon radicals which may contain hetero atoms, and at most two of the three substitutents R may be hydrogen atoms. The hetero atoms can be all atoms except carbon atoms and hydrogen atoms, preferably N, O, F, Si, P, S, Cl, Br, Sn and I.

The phosphonites are esters of phosphorus acid, and are represented by the formula P(OR)$_3$R, wherein R has the same definitions described above, or may be halogen. The phosphites or phosphonites of this invention are preferably a solid at 20° C., and are usually a crystalline solid.

Examples of the phosphites of this invention are tri (dimethylphenyl)phosphite, tri(t-octylphenyl)phosphite, tri (nonylphenyl)phosphite (ab. TNPP), tri(docosanylphenyl) phosphite, monobutyl-dioctyl phosphite, tribenzyl phosphite, monobutyl-diphenyl phosphite, mono nonylphenyl-dioctyl phosphite, monohexyl-diisopropyl phosphite, cyclohexyl-dioctadecyl phosphite, diphenyl-neopentyl diphosphite, diisooctyl-octylphenyl phosphite, tetrakis(nonylphenyl)propylene glycol diphosphite, heptakis (dipropylene glycol)triphosphite, poly(dipropylene glycol) phenyl phosphite, bis-stearyl pentaerythritol diphosphite (ab. BSPDP), 2,2-dimethylpropanol diphosphite, dilauryl hydrogen phosphite, dioctyl hydrogen phosphite, dioctadecyl hydrogen phosphite, trimethylol propane phosphite, 2,2-dimethyl-1,3 propylene lauryl phosphite, triphenyl phosphite, tricyclohexyl phosphite, triethyl phosphite, trioctyl phosphite, trihexyl phosphite, tridodecyl phosphite, trioctadecyl phosphite, triisopropyl phosphite, tri-tertiary butyl phosphite, tri-2-ethylhexyl phosphite, tricresyl phosphite, diphenyl 2-ethylhexyl phosphite, triphenyl phosphite, tris(2,5-di-tert-butylphenyl)phosphite, tris(2-tert-butylphenyl)phosphite, tris(2-phenylphenyl)phosphite, tris(2 (1,1-dimethyl)phenyl)phosphite, tris(2-cyclohexylphenyl)phosphite, tris(2-tert-butyl-4-phenylphenyl)phosphite, tris(2-tert-butyl-4-methylphenyl) phosphite, tris(2,4 di-tert-amylphenyl)phosphite, tris(2,4-di-tert-butylphenyl)phosphite, bis(2,4-di-tert-butylphenyl) pentaerythritol diphosphite, bis-stearyl pentaerythritol diphosphite, tri(mixed mono- and dinonylphenyl)phosphite, 4,4'-isopropylidene-diphenol alkyl (C$_{12}$–C$_{25}$)phosphite, diphenyl isodecyl phosphite, and diphenyl isooctyl phosphite.

Examples of the phosphonites of this invention are phenyl diethyl phosphonite, octyl dibutyl phosphonite, decyl diisopropyl phosphonite, hexyl di-tertiary butyl phosphonite, dodecyl dioctyl phosphonite, cyclohexyl dioctadecyl phosphonite, lauryl diphenyl phosphonite, phenyl dicyclohexyl phosphonite, nonylphenyl di-nonylphenyl phosphonite, stearyl di benzyl phosphonite, and dioctyl neopentyl di-phosphite.

Examples of the acid-binding metal salts of this invention are metal carbonate, metal bicarbonate, metal carboxylate, metal oxide, metal hydroxide, metal phosphite, metal borate, metal hydrotalcite, metal zeolite, and mixtures thereof. Examples of the metal contained in the aforesaid metal salts are selected from group I A, II A, III A, IV A, or rare earth of the periodic table. Preferably, the acid-binding metal salts are selected from a group consisting of aluminum oxide (Al$_2$O$_3$), talc, hydrotalcite, zeolite, silica, montmorillonite, bentonite, MgO, CaO, rare earth oxides, Mg(OH)$_3$, Ca(OH)$_2$, Ca$_2$O$_3$, calcium acetate, and aluminum magnesium borate, preferably zeolite and hydrotalcite, and most preferably zeolite-containing acid-binding metal salts.

Suitable zeolites of this invention are those having the following formula (II):

$$XM^N[x(AlO_2).y(SiO_2)].w(H_2O) \qquad (II)$$

wherein N is the cation valency of M. M is a metal selected from group I A or II A of the periodic table, particularly from sodium, potassium, magnesium and/or calcium. The y/x is a number between 0.8 to 1.2, and w is a number between 0.5 to 50.

Examples of the suitable zeolite are those having the following empirical formula:

$$12Na[12(AlO_2).12(SiO_2)].12(H_2O)$$

$$4.5Ca.3Na[12(AlO_2).12(SiO_2)].30(H_2O)$$

$$9K.3Na[12(AlO_2).12(SiO_2)].27(H_2O)$$

Suitable types of zeolite of this invention are A, X, Y, L, ZSM5, 11, 22, and 23 types of Mordenite, Offretite, gray cross zeolite, sodalite, organic zeolite, and ALPO or SAPO substances, preferably A, X, Y types zeolite, more preferably A types zeolite.

The acid binding metal salt treated with the surface conditioning agent is dispersed in the organic phospite or phosphonite with a particle size less than 50 μm, preferably less than 20 μm, more preferably less than 2 μm. If the particle size of the acid-binding metal salts is greater than 100 μm, the stability to hydrolysis will be poor, especially at a high temperature and a high atmospheric humidity condition.

The hydrotalcite used in this invention are those having the following formula (III):

$$(1-x)M^{(2-)}.xM^{(3-)}.2(OH).(x/n)A^{(n-)}.pH_2O \qquad (III)$$

wherein M$^{(2-)}$ represents Mg, Ca, Cs, Ba, Zn, Pb, and/or Ni. M$^{(3+)}$ represents Al, B, or Bi. A$^{(n-)}$ is the anion valency, n is a number from 1 to 4, x is a number from 0 to 0.5, and p is a number from 0 to 2. The A can be $OH^{31}$, $Cl^-$, $Br^-$, $I^-$, $ClO_4^-$, $HCO_3^-$, $CH_3COO^-$, $C_6H_5COO^-$, $CO_2^{-2}$, $SO_4^{-3}$, $(CHOHCOO)_2^{-2}$, $(CHOH)_4CH_2OHCOO^-$, $C_2H_4(COO)_2^{2-}$, $(CH_2COO)_2^{-2}$, $CH_3CHOHCOO^-$, $SiO_3^{-2}$, $SiO_4^{-4}$, $Fe(CN)_6^{-3}$, $Fe(CN)_6^{-4}$, $BO_2^{-3}$, $PO_3^3$, or $HPO_4^{-2}$.

Other hydrotalcite which can be used conveniently in this invention are those having the following formula (III a):

$$xM^{(2+)}.Al_2.(2x+Gnz)(OH).2A^{(n-)}.pH_2O \quad \text{(III a)}$$

wherein $M^{(2+)}$ of formula (III a) is selected at least from one of the metal group similar to Mg or Zn, preferably Mg. The $A^{(n-)}$ is an anion, particularly selected from $CO_3^{2-}$ and $S_2^-$. The valency of the above described anion is n. p is a number, preferably from 0.5 to 5. X and z are both integers, wherein x is preferably from 2 to 6, and wherein z is preferably smaller than 2.

Preferable hydrotalcites of this invention are those compounds having formula (III), wherein $M^{(2+)}$ is Ca or Mg, or solid solution of Mg or Zn, the $A^{(n-)}$ is $CO_3^{2-}$, $BO_3^{(3-)}$, or $PO_2^{(2-)}$, x is a number from 0 to 0.5, p is a number from 0 to 2, and the $M^{(3+)}$ of these metal salts is preferably an aluminum ion.

Results from experiments show that the hydrotalcites particularly suitable for this invention are those of compounds with the following formulas:

| | |
|---|---|
| $Al_2O_3.6MgO.CO_2.12H_2O$ | (III b), |
| $4.5Mg.Al_2(OH)_{13}.CO_3.3.5H_2O$ | (III c), |
| $4MgO.Al_2O_3.2CO_2.9H_2O$ | (III d), |
| $4MgO.Al_2O_2.2CO_2.6H_2O$ | (III e), |
| $ZnO.MgO.Al_2O_3.CO_2.8–9H_2O$ | (III f), or |
| $ZnO.3MgO.Al_2O_3.CO_2.5–6H_2O$ | (III g) |

As mentioned hereinbefore, the surface conditioning agent of this invention is selected from the group consisting of silane coupling agents, titanate coupling agents, zirconate coupling agents, aluminate coupling agents, zirco-aluminate coupling agents, non-ionic surfactants, and anionic surfactants. The surface conditioning agent is preferably selected from silane coupling agents and non-ionic surfactants, and is most preferably a silane coupling agent. Examples of titanate coupling agents are isopropyl triso stearoyl titanate, isopropyl tris(dioctyl pyrophosphate)titanate, bisdioctyl (pyrophosphate) oxyacetate titanate, bisoctyl (pyrophosphate)ethylene titanate, tetraisopropyl bis(dioctyl phosphite)titanate, and tetra octyl bis(di(tridecyl phosphite)) titanate.

Specific examples of the silane coupling agents are γ-aminopropyl trimethoxy silane, γ-aminopropyl triethoxy silane, γ-aminopropyl methyl diethoxy silane, N-β-aminoethyl γ-aminopropyl trimethoxy silane, N-β-aminoethyl-γ-aminopropyl methyl dimethoxy silane, 4,5-dihydro-1-[3-(triethoxysilyl)propyl]imidazole, γ-mercaptopropyl trimethoxy silane, γ-mercaptopropyl methyldimethoxy silane, γ glycidyloxypropyl trimethoxy silane, γ-methacryloxypropyl trimethoxy silane, γ-chloropropyl trimethoxy silane, γ-chloropropyl triethoxy silane, γ-chloropropyl methyl dimethoxy silane, vinyl trimethoxy silane, vinyl triethoxy silane, and vinyl tris(β-methoxy ethoxy)silane, preferably vinyl trimethoxy silane and the like.

Specific examples of the non-ionic surfactants are propylene glycol stearate, di-stearo-propylene glycol, di-ethylene glycol-mono-stearate, sesqui-oleo-sorbitant, tri-stearo sorbitant, mono-palmito-polyethylene glycol, polyethylene glycol, polypropylene glycol, di-stearo-polyethylene glycol, di-oleo-polyethylene glycol, lano fatty acid polyethylene glycol, tri-stearoamide polyoxyethylene sorbitant, polyoxyethylene lano ether alcohol, polyoxyethylene coconut fatty acid amide, polyoxyethylene polypropylene glycol, polyoxyethylene alkyl ether, polyoxyethylene polyoxypropylene alkyl ether, coconut fatty acid mono-ethanolamide, stearo-ethanolamide, and stearo-di-ethanolamide, polyoxyethylene phenyl ether (the hydrogen atom of the benzene ring can be substituted with groups such as isobutyl or octyl group), polyoxyethylene octyl phenyl ether, and the like, preferably polyoxyethylene alkyl ether, polyoxyethylene polyoxypropylene alkyl ether, and polyoxyethylene phenyl ether.

Specific examples of anionic surfactants include alkyl sodium sulfate, polyoxyethylene alkyl ether sodium sulfate, polyoxyethylene alkyl phenyl ether sodium sulfate, phosphoric polyoxyethylene alkyl ether, phosphoric polyoxyethylene alkyl phenyl ether, phosphoric triethanoamine polyoxyethylene alkyl phenyl ether, and lecithin.

The total amount of the above described surface conditioning agent and the acid-binding metal salt is 100% by weight. The weight ratio of the surface conditioning agent to the acid binding metal salt is in the range of 0.1 to 50%:99.5 to 50%, preferably 2 to 25%:98 to 75%. When the weight ratio of the surface conditioning agent to the acid binding metal salt is below 0.1:99.9, the dispersion of the acid-binding metal salt in the organic phosphorous containing antioxidant and the stability to hydrolysis will be poor. When the weight ratio for these two compounds is above 50:50, it will become uneconomical.

The process for the preparation of the acid-binding metal salt treated with the surface conditioning agent includes the step of placing the acid-binding metal salt, such as zeolite, hydrolcite and the like, with the surface conditioning agent into a closed mixer to uniformly mix them together to ensure formation of an encapsulation on the surface of the zeolite or the hydrotalcite. In another method, the zeolite or the hydrotalcite is slurried by mixing with a solvent, and is subsequently mixed uniformly with the surface conditioning agent. This mixture is then dried to eliminate the solvent. The operating condition for this method is desired to be below 100° C.

The organic phosphorus-containing antioxidant stabilized against hydrolysis of this invention can be modified by mixing the organic phosphite (or phosphonite) and the acid binding metal salt, which is treated with a surface conditioning agent, with a carrier for improving processability of the styrenic resin composition during compounding and extruding operation. The incorporation of the carrier can be accomplished by pressing, extrusion or pelletizing. Basically, there is no limitation for the carrier to be used in this invention. The carrier is preferably made from an organic compound which exhibits a melting point that is higher than that of the organic phosphorus containing antioxidant. Examples of the carrier are lubricants, processing aids, primary antioxidant and secondary antioxidant. Examples of lubricants are polypropylene wax, polyethlene wax, and ethylene bis-stearamide (EBA). Examples of secondary antioxidant are sulfur containing compound and sterically hindered amine-containing compound. Primary antioxidant can be phenolic antioxidants, such as tetra kis methylene-3-(3',5'-di-tert-butyl-4-hydroxyphenyl) propionate methane. The amount of the above described carrier to be added is about 0 to 200 parts per 100 parts of the organic phosphorus-containing antioxidant, and preferably about 25 to 150 parts.

Another object of this invention is to add an organic polymer into the organic phosphorus-containing antioxidant which has been stabilized against hydrolysis, so as to produce a thermoplastic resin composition which possesses good stability to hydrolysis, better initial color, and excellent thermal stability during processing. Examples of the above described organic polymers are ethylenic polymer, styrenic polymer, diene polymer, polycarbonate, polyester, and mixtures thereof, wherein the ethylenic polymer are those compounds such as polypropylene(PP), polyethylene(PE), polyvinyl chloride(PVC), and polymethylmethacrylate(PMMA). The styrenic polymer are those compounds such as polystyrene(PS), high impact polystyrene(HIPS), acrylonitrile-butadiene-styrene (ABS) copolymer, acrylonitrile-styrene (AS) copolymer, methylmethacrylate-butadiene-styrene (MBS) copolymer, acrylate-acrylonitrile-styrene (AAS) copolymer, and ethylene-propylene-diene-rubber-acrylonitrile-styrene (AES) copolymer. The diene polymer are those compounds, such as homopolymers or copolymers of butadiene, isopentadiene and chlorobutadiene. The polyester are those compounds, such as polyethylene terephthalate (PET) and polybutylene glycol terephthalate (PBT).

The organic polymer of this invention for extrusion contains greater than 2% water. The thermoplastic resin composition can be obtained by adding a suitable amount of the carrier into the above described organic polymer (i.e., a styrenic resin having a water content greater than 2% by weight) with the stabilized organic phosphite or phosphonite (i.e., an organic phosphorous-containing antioxidant) in a predetermined ratio, and extruding the mixture to form pellets using an extruder which is provided with a devaporization device (i.e., Vent port). The operating temperature of the above described extruder is adjusted to a temperature of 180 to 300° C. The above described organic polymer emulsion can be obtained by coagulation, and is subsequently dewatered via a centrifugal dewatering device to form a polymer powder with about 30 wt % of water. In order to simplify the operating steps for the drying operation, the above described polymer powder with 30 wt % water content is normally added directly with the carrier additives and other polymers, and is subsequently compounded and dewatered to form a polymer product with a water content of below 0.5 wt %.

The stabilized organic phosphorus-containing oxidant of this invention is particularly suitable for use in resin processing at a high temperature and a high humidity condition, more particularly for compounding and extruding at a temperature above 180° C., preferably above 200° C. At such operating condition, the hydrolysis of the phosphorous-containing antioxidant is little. In addition, excellent initial color and thermal stability of the resin are also obtained.

The inventors found that by mixing the organic phosphite or phosphonite with the acid-binding metal salt treated with a surface conditioning agent to form the phosphorous containing antioxidant prior to blending or compounding with the styrenic resin having a water content greater than 2 wt % (preferably greater than 5 wt %), the aforesaid hydrolysis problem as encountered in the prior art can be eliminated. That is, it is important to mix the organic phosphites or phosphonites with the acid-binding metal salt treated with a surface conditioning agent in advance, without the presence of the styrenic resin. It was found that the aforesaid hydrolysis problem will be encountered if the acid-binding metal salt is not treated with a surface conditioning agent and if (a) the organic phosphite or phosphonite and (b) the acid-binding metal salt treated with the surface conditioning agent are not mixed to form a uniform mixture prior to mixing or compounding with the styrenic resin. The mechanism of the interaction between the organic phosphite or phosphonite and the acid-binding metal salt treated with the surface conditioning agent which are mixed prior to mixing or compounding with the styrenic resin is not yet clear. It is assumed that a strong binding between the two compounds occurs prior to mixing or compounding with the styrenic resin, thereby significantly enhancing the stability to hydrolysis for the phosphorous-containing antioxidant. On the other hand, a relatively weak binding between the two compounds exists in the mixture due to direct dispersion of the two compounds into the styrenic resin without prior mixing of the two compounds, thereby significantly reducing the enhancing effect of the acid-binding metal salt treated with the surface conditioning agent to the stability to hydrolysis of the phosphorous-containing antioxidant.

The styrenic resin composition prepared according to the process of this invention preferably contains 0.01–5.0 parts of the phosphorous-containing antioxidant and more preferably contains 0.02–2.0 parts of the phosphorous-containing antioxidant based on 100 parts of the styrenic resin (dry base).

As mentioned hereinbefore, the rubbery graft copolymer (A) is prepared by emulsion graft polymerization of 50 to 90 wt % of vinyl aromatic monomers, 10 to 50 wt % of vinyl cyanide monomers, and 0 to 40 wt % of copolymerizable monomers in the presence of rubbery polymer latex to form a rubbery graft copolymer (A) latex. The latex is subsequently subjected to coagulation to form a slurry which is then dewatered to form a powdery rubbery graft copolymer (A) with a water content of 5–50 wt %, preferably 10–40 wt %, and more preferably 15–35 wt %. The rubber content of the emulsion polymerized rubbery graft copolymer (A) is generally 15–85 wt %, and preferably 45–80 wt %.

Examples of the coagulant for coagulation of the rubbery graft copolymer (A) includes $CaCl_2$, $MgSO_4$, $H_2SO_4$, HCl, and the like. The coagulation temperature is preferably in a range of 25 120° C., and preferably 40–105° C. Steam can be used to aid coagulation of the rubbery graft copolymer (A).

Examples of the dewatering device are belt filter, centrifuge filter, and screw-type dewatering machine.

Examples of the rubbery polymer used in the present invention are dienic rubbery polymer, acrylic rubbery polymer, olefin rubbery polymer, silicone rubbery polymer, and silicone-acrylic rubbery polymer. The rubbery polymer has a glass transition temperature of not greater than 10° C. Dienic rubbery polymer includes a homopolymer or copolymer prepared from 100 to 60 wt % of conjugated diene monomer and 0 to 40 wt % of copolymerizable monomer (such as styrene, acrylonitrile etc.). Acrylic rubbery polymer includes a homopolymer or copolymer mainly composed of alkylesters of acrylic acid or alkylesters of methacrylic acid.

Examples of olefin rubber polymer are ethylene-propylene copolymer, EPDM, etc.

Silicone or silicone-acrylic rubbery polymer contains mainly silicone or silicone/acrylic structures in the main chain.

Examples of the dienic rubbery polymer are polybutadiene, butadiene-styrene copolymer, butadiene-acrylonitrile copolymer, isoprene-butylacrylate copolymer and butadiene-methyl methacrylate copolymer. Specifically, the dienic rubbery polymer latex having a weight average particle size of 0.05 to 0.8 $\mu$m may be directly polymerized from the above dienic monomers and copolymerizable monomers. Alternatively, a dienic rubbery polymer latex having a small particle size of 0.05 to 0.18 μm may be preliminarily prepared, and is subsequently subjected to agglomeration by conventional agglomerating methods to form a dienic rubbery polymer latex having a weight average particle size of 0.2 to 0.8 μm. The agglomerating method includes chemical agglomerating method, mechanical agglomerating method, and freezing agglomerating method.

The chemical agglomerating method involves adding an organic acid, a metal salt or a polymeric agglomerating agent containing carboxylic acid group into the butadienic rubbery polymer latex. Butyl acrylate-methacrylic acid copolymer may be used as the polymeric agglomerating agent in the chemical agglomerating method.

Examples of the styrenic monomer of the present invention are styrene, α-methyl styrene, para-chlorostyrene, para-tert-butyl styrene, para-methyl styrene, ortho-chlorostyrene, para-chlorostyrene, 2,5-dichlorostyrene, 3,4-chlorostyrene, 2,4,6-tribromostyrene and 2,5-dibromostyrene. Styrene and α-methyl styrene are preferred.

Examples of the vinyl cyanide monomer of the present invention are acrylonitrile and α-methyl acrylonitrile. Acrylonitrile is preferred.

Examples of the copolymerizale monomer used for preparing the rubbery graft copolymer (A) are esters of acrylic acid, esters of methacrylic acid, maleimide-based monomer, acrylic acid, methacrylic acid, maleic anhydride, and ethylene glycol methacrylate. Examples of esters of methacrylic acid are methyl methacrylate, ethyl methacrylate, propyl methacrylate, butyl methacrylate, benzyl methacrylate, hexyl methacrylate, cyclohexyl methacrylate, dodecyl methacrylate, and 2-hydroxyethyl methacrylate. Methyl methacrylate is preferred. Examples of esters of acrylic acid and methyl acrylate, ethyl acrylate, propyl acrylate, and butyl acrylate. Butyl acrylate is preferred.

Examples of maleimide based monomer are maleimide, N-methyl maleimide, N-isopropyl maleimide, N-butyl maleimide, N-hexyl maleimide, N-octyl maleimide, N-dodecyl maleimide, N-cyclohexyl maleimide, N-phenyl maleimide, N-2,3 dimethyl phenyl maleimide, N-2,4-dimethyl phenyl maleimide, N-2,3-diethyl phenyl maleimide, N-2,4-diethyl phenyl maleimide, N 2,3-dibutyl phenyl maleimide, N-2,4-dibutyl phenyl maleimide, N-2,6-dimethyl phenyl maleimide, N-2,3-dicholophenyl maleimide, N-2,4-dicholophenyl maleimide, N-2,3-dibromophenyl maleimide, and N-2,4-dibromophenyl maleimide. N-phenyl maleimide is preferred.

As described above, the styrenic copolymer (B) is prepared by copolymerization of 50–90 wt % of styrenic monomer, 10 to 50 wt % of vinyl cyanide monomer, and 0 to 40 parts by weight of copolymerizable monomer. Examples of the styrenic monomer, the vinyl cyanide monomer, and the copolymerizable monomer are those mentioned hereinbefore. The styrenic copolymer (B) may be prepared by bulk, solution, suspension or emulsion polymerization. Bulk or solution polymerization is preferred. The weight average molecular weight of the styrenic copolymer (B) is in the range of 60,000 to 400,000. The number average weight of the styrenic copolymer (B) is in the range of 30,000 to 200,000. The thus formed bulk or solution polymerized styrenic copolymer (B) is normally free of water. However, the styrenic copolymer (B) can absorb moisture when exposed to the atmosphere, and can contain up to 0.3 wt % water when exposed to the atmosphere for a long period.

The styrenic resin composition from the extruder according to the process of this invention preferably has a water content of less than 1% by weight, more preferably less than 0.5% by weight, and most preferably less than 0.3% by weight.

The organic phosphorous-containing antioxidant can be mixed with the styrenic resin in a mixer, such as Henschel mixer and tumbler mixer, prior to feeding into the extruder. Additives can be added into the mixer to blend with the organic phosphorous-containing antioxidant and the styrenic resin. The organic phosphorous-containing antioxidant and the styrenic resin can also be separately fed into the extruder.

The extruder employed according to the process of this invention preferably includes a kneading section, a vent section, and a pumping section. The extruder is preferably operated at a temperature in a range of 180–300° C., and more preferably 200–300° C.

The following examples illustrate the practicality of this invention, and are not intended to limit the scope of this invention and the appended claims.

EXAMPLES

Examples 1 and 2 and Comparative Example 1

Stability to Hydrolysis Test on Antioxidant

Since the pH value will decrease in view of the generation of the phosphorus acid from the hydrolysis, the rate of the hydrolysis can be obtained by measuring the variation of the pH value.

A one-liter flask was provided with a thermometer, a mechanical stirrer, a condenser, and a pH meter. Successively, 450 g of the deionized water and 50.0 g (0.100 mole) of tri(nonylphenyl)phosphite (TNPP used as the phosphite compound) with the aluminum oxide or zeolite (used as the acid-binding metal salt), which has been treated with silane serving as the surface conditioning agent, were introduced into the flask. The stirrer was started, and the mixture was heated to a predetermined temperature of 80° C. by a heater. The pH value was recorded every hour.

The stability test result is shown in Table 1. The weight ratio of the silane to the aluminum oxide is 1:10, and that of the silane to the A-type zeolite is also 1:10. The average particle size is 0.5 μm.

TABLE 1

| Composition | Comparative Example 1 | Example 1 | Example 2 |
|---|---|---|---|
| TNPP | 50 | 50 | 50 |
| Deionized water | 450 | 450 | 450 |
| Aluminum oxide(*) | — | 2.75 | — |
| Zeolite(*) | — | — | 2.75 |
| Stability against hydrolysis | X | ○ | ○ |

(*)treated with silane as the surface conditioning agent.

The symbol "X" indicates poor stability to hydrolysis, whereas the symbol "O" indicates good stability to hydrolysis.

Figure 1:
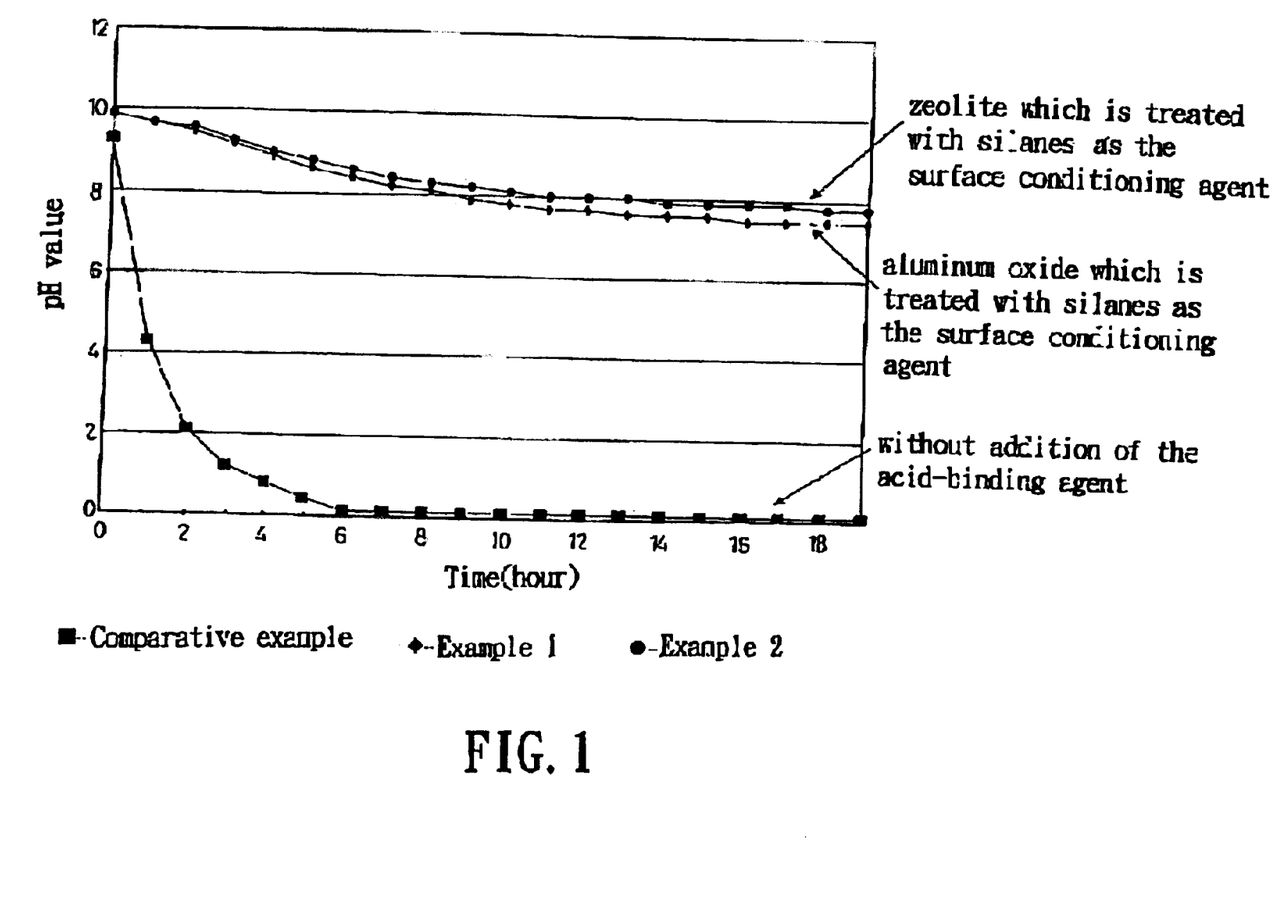
FIG. 1 is a diagram illustrating pH values for the Examples of this invention and the Comparative Example for different phosphorous-containing antioxidants.

The variation of the pH value is illustrated in FIG. 1. The curve shown in FIG. 1 indicates that the composition of the antioxidant of this invention is capable of effectively deferring the rate of hydrolysis.

Examples 3 and 4 and Comparative Examples 2 to 5

Stability to Hydrolysis Test on Antioxidant

Bis-stearyl pentaerythritol diphosphite (BSPDP) was used as the phosphite compound and was uniformly mixed with different acid-binding agents and Irganox 1010 (used as the carrier) according to the composition shown in Table 2

(different codes are given to respectively represent the samples in Table 2). The mixture was subsequently heated and extruded to form into pellets. The resulting products were then prepared for a physical property test. A one-liter flask, which is similar to Example 1, was provided with a temperature controller, a mechanical stirrer, a condenser, and a pH meter. Five hundreds grams of deionized water was introduced into the flask, and was heated to and sustained at a temperature of 100° C. Afterwards, 10 g of the products to be tested were added into the flask. The initial pH value (0 min) was recorded, and was then recorded every 15 mins. The results are shown in Table 3.

TABLE 2

| Types of antioxidant | A | B | C | D | E | F | G | H | I |
|---|---|---|---|---|---|---|---|---|---|
| DGPDP | 40 | 40 | 40 | 40 | 40 | 100 | 50 | 0 | 50 |
| Irganox 1010[(1)] | 40 | 40 | 40 | 40 | 40 | 0 | 50 | 0 | 0 |
| Irgafos 168[(2)] | | | | | | | | 100 | |
| DHT-4A-3[(*3)] | | | | 20 | | | | | |
| X type zeolite[(#)] | | | | | 20 | | | | |
| A type zeolite[(#4)] | 20 | | | | | | | | |
| DHT 4A-2[(#7)] | | 20 | | | | | | | |
| MgO + DHT-4A-2[(#5)] | | | 20 | | | | | | |
| EBA [(**6)] | | | | | | | | | 50 |

[(*)]not treated with silane.
[(#)]treated with silane.
[(**)]lubricant.
[(1)]Irganox 1010 is a trade name and is available from Ciba geigy Chemicals Corporation. Its chemical name is tetra kis methylene-3-(3',5'-di-tert-butyl-4-hydroxyphenyl) propionate methane.
[(2)]Irgafos 168 is a trade name and is available from Ciba geigy Chemicals Corporation. Its chemical name is tris (di-tert-butyl-2,4 phenyl) phosphite.
[(3)]DHT-4A-2 is available from Kyowa company. Its chemical name is 4.5 $Mg.Al_2(OH)_{13}.CO_3.3.5H_2O$.
[(4)]A type zeolite treated with silane has a weight ratio of silane to A type zeolite of about 2:18. Its weight average particle size is 0.5 μm.
[(5)]MgO and DHT-4A-2 are mixed and surface treated with silane. The weight ratio of MgO plus DHT-4A-2 to silane is 17:3. MgO is available from Kyowa company and has a trade name Kyowaway 150.
[(6)]EBA is ethylene bis-stearamide.
[(7)]DHT 4A 2 treated with silane has a weight ratio of silane to DHT 4A 2 of about 2:18.

TABLE 3

| | | | Sample number | | | |
|---|---|---|---|---|---|---|
| | | Example 3 | Example 4 | Comp. Example 2 | Comp. Example 3 | Comp. Example 4 | Comp. Example 5 |
| Types of antioxidant | | A | C | D | E | F | O |
| measured pH value | 0 min | 7.8 | 8.0 | 3.6 | 5.4 | 2.5 | 6.5 |
| | 15 min | 7.6 | 7.3 | 4.0 | 5.0 | 1.7 | 2.3 |
| | 30 min | 7.3 | 6.9 | 3.4 | 4.0 | 1.6 | 2.1 |
| | 45 min | 7.0 | 6.2 | 3.0 | 3.8 | 1.5 | 1.6 |
| Stability to hydrolysis | | ○ | ○ | X | X | X | X |

The stability to hydrolysis is better when the variation of the pH value as described above is smaller and the pH value is higher. The composition of the antioxidant of this invention (Examples 3 and 4) exhibits good stability to hydrolysis. Comparative Example 2 employed DHT 4A-2 type hydrotalcite. However, since such hydrotalcite was not treated with the silane, the stability to hydrolysis is thus poor. Comparative Example 3 employed the X type zeolite which was not treated with silane. Due to large particle size (average particle size is 60 μm), the mixing of the BSPDP and the Irganox 1010 is poor, thereby resulting in poor stability to hydrolysis. Comparative Example 4 employed only BSPDP without addition of the acid-binding agent. Comparative Example 5 employed both the BSPDP and the Irganox 1010 without addition of the acid-binding agent. Both Comparative Examples 4 and 5 also exhibit poor stability to hydrolysis.

Examples 5 to 8 and Comparative Examples 6 to 10

Stability to Hydrolysis Test on the Styrenic Resin Composition

The measuring standard for the stability to hydrolysis of the composition of this invention in a resin is based on yellow index (YI) value.

Preparation of Rubbery Graft Copolymer (A)

A synthetic rubber latex was first prepared by reacting the following components:

| components | weight parts |
|---|---|
| 1,3-butadiene | 150.00 |
| potassium persulfate solution | 15.00 |
| potassium oleate | 2.00 |
| distilled water | 190.00 |
| ethylene glycol methacrylate | 0.13 |

The reaction was carried out at 65° C. for 12 hours to yield the synthetic rubber latex with a conversion of monomer of 94% and a weight average particle size of 0.1 μm. The solid content of the synthetic rubber latex is 40%.

A polymeric agglomerating agent containing carboxylic acid group was then prepared by reacting the following components:

| components | weight parts |
|---|---|
| ethyl acrylate | 90.0 |
| methacrylic acid | 10.0 |
| potassium persulfate solution (1%) | 0.5 |
| sodium dodecyl sulfate solution (10%) | 1.0 |
| n-dodecyl mercaptan | 1.0 |
| distilled water | 200.0 |

The reaction was carried out at 75° C. for 5 hours to yield the polymeric agglomerating agent with a conversion of monomer of 95% and a pH value of 6.0.

100 parts by weight (dry weight) of the synthetic rubber latex was then agglomerated with 3 parts by weight (dry weight) of the polymeric agglomerating agent to produce an agglomerated rubber latex having a pH value of 8.5 and a weight average particle size of about 0.31 μm.

The rubbery graft copolymer (A) was then prepared by graft polymerization of a reaction mixture according to a recipe as follows:

| components | weight parts |
|---|---|
| agglomerated rubber latex (dry weight, 0.31 μm) | 100.0 |
| styrene | 25.0 |
| acrylonitrile | 8.3 |
| potassium oleate | 1.2 |
| tert-dodecyl mercaptan | 2.0 |

-continued

| components | weight parts |
|---|---|
| cumene hydroperoxide | 3.0 |
| ferrous sulfate solution (0.2%) | 3.0 |
| Rongalite solution (10%) | 0.9 |
| Ethylene diamine tetraacetic acid Solution (0.25%) | 3.0 |
| Distilled water | 200.0 |

The thus-formed rubbery graft copolymer (A) latex was then coagulated with calcium chloride ($CaCl_2$), and was subsequently dewatered to recover a powdery rubbery graft copolymer (A-2) having a water content of 30 wt %. The wet rubbery graft copolymer (A-2) was then dried in a dryer with heated air at 56° C. such that the dried rubbery graft copolymer (A-1) had a water content of less than 0.5 wt %.

lubricant ethylene bis-stearamide(EBA). These mixtures were then extruded using a Germany W&P ZSK-25 extruder at a temperature of 230° C. Each of the thus-formed styrenic resin compositions was in pellet-form, and had a water content of less than 0.3 wt %. It is desirable to devolatilize the water during the extrusion of the styrenic resin composition. The pellets of these polymer were injected, via a Taiwan 4OZ SM-90 injection machine, at a temperature of 210° C., to make discs with a diameter of 55 mm and a thickness of 3.2 mm. These discs were cooled, and were subsequently analyzed for their YI value via a Gretoawacbeth color-eye 3100 spectrometer. After the analysis, these discs were placed into a rotatable tray-type oven for heating for two hours at a temperature of 180° C., and were subsequently cooled and analyzed for their YI value. The difference between the YI values before and after the heating in the oven is $\Delta YI$. The smaller the YI and the $\Delta YI$, the better will be the stability to hydrolysis. The results are shown in Table 4.

TABLE 4

| | | Samples No. | | | | | | | | |
|---|---|---|---|---|---|---|---|---|---|---|
| | | Examples | | | | Comparative Examples | | | | |
| | | 5 | 6 | 7 | 8 | 6 | 7 | 8 | 9 | 10 |
| Rubbery graft copolymer (A-1) (dry base)(*) parts | | | | 30 | 30 | | | | | |
| Rubbery graft copolymer (A-2) (dry base)(**) parts | | 30 | 30 | | | 30 | 30 | 30 | 30 | 30 |
| Styrenic copolymer (B) parts | | 70 | 70 | 70 | 70 | 70 | 70 | 70 | 70 | 70 |
| Lubricant EBA parts | | 2 | 2 | 2 | 2 | 2 | 2 | 2 | 2 | 2 |
| Antioxidant | Types | A | H | A | B | E | F | G | H | I |
| | Parts | 0.15 | 0.15 | 0.15 | 0.15 | 0.15 | 0.15 | 0.15 | 0.15 | 0.15 |
| YI value | YI | 13 | 13 | 11.5 | 12.4 | 15.2 | 18 | 16 | 17 | 19 |
| | $\Delta YI$ | 30 | 30 | 29 | 28 | 36 | 39 | 38 | 36 | 40 |

(*)Rubbery graft copolymer (A-1) is acrylonitrile-butadiene styrene copolymer (dry powder) with less than 0.5% of water by weiqht.
(**)Rubbery graft copolymer (A 2) is acrylonitrile-butadiene-styrene copolymer (wet powder) with 30% of water by weight.
Note:
the styrenic resin which is fed to the extruder contains 11.3 wt % of water in Examples 5, 6 and Comparative Examples 6, 7, 8, 9, 10, based on the total weight of the dry styrenic resin and its water content which comes from wet powdery rubbery graft copolymer (A 2).

Preparation of Styrenic Copolymer (B):
Acrylonitrile Styrene Copolymer

In a continuous polymerization process, 12 kg/hr of a composition of styrene (78 wt %) and acrylonitrile (22 wt %), 3.0 g/hr of ethylene bis-stearamide (EBA), and trace amount of benzoyl peroxide and tert-dodecyl mercaptan were added into a 45 liters reactor. The reaction was carried out at a temperature of 108° C. in the presence of toluene which serves as a solvent and which is in an amount of about 15 wt % based on total weight of the mixture in the reactor. The conversion was maintained at a constant rate of about 55%. The reaction effluent was subjected to a purification process to obtain a product of the styrenic copolymer (B).

The rubbery graft copolymer (A-2) with 30% water, the rubbery graft copolymer (A-1) with less than 0.5% water, and the styrenic copolymer (B) (i.e. acrylonitrile styrene copolymer) were employed separately for preparation of different styrenic resin compositions for the test, and each of which was added with a selected one of the antioxidant (each is represented by a code number) shown in Table 2 and The results shown in Table 4 indicate that the phosphorus-containing antioxidant of the Comparative Examples lost its antioxidative property after being hydrolyzed. The values of the YI and the $\Delta YI$ of the composition of the antioxidant of this invention are better than those of the Comparative Examples, thereby increasing the antioxidative property of the resins, and thereby preventing the phosphite compounds from hydrolyzing. The antioxidative property of the antioxidant of this invention is considerably enhanced, and is useful for the industry.

Comparative Example 11

30 parts by weight (dry base) of rubbery graft copolymer (A-2) (with a water content of 30 wt %), 70 parts by weight (dry base) of styrenic copolymer(B), 2 parts by weight of EBA, 0.06 parts by weight of BSPDP, 0.06 parts by weight of Irganox 1010, and 0.03 parts by weight of A type zeolite (10 wt % silane treated) were added into a Henschel mixer for forming a mixture. The mixture having a water content of 11.3 wt %, based on the total weight of the styrenic resin and its water content, was subsequently extruded using a W&P ZSK-25 extruder at a temperature of 230° C. to obtain a product of the styrenic resin composition. The values of YI and ΔYI of the thus-formed product were determined, and were found to be equal to 14 and 35, respectively. The Comparative Example 11 shows that without prior mixing of BSPDP and A type zeolite (10 wt % silane treated), the values of YI and ΔYI of the styrenic resin composition are worse.

Comparative Example 12

Similar to Comparative Example 11, 30 parts by weight (dry base) of the rubbery graft copolymer (A-2) (with a water content of 30 wt %), 70 parts by weight (dry base) of the styrenic copolymer(B), 2 parts by weight of EBA, 0.06 parts by weight of BSPDP, 0.06 parts by weight of Irganox 1010, and 0.03 parts by weight of DHT-4A-2 (10 wt % silane treated) were added into a Henschel mixer to form a mixture. The blended mixture having a water content of 11.3 wt %, based on the total weight of the styrenic resin and its water content, was subsequently extruded using a mixer W&P ZSK-25 extruder at a temperature of 230° C. to form a product of the styrenic resin composition. The values of YI and ΔYI of the thus-formed product are determined, and were formed to be equal to 15.5 and 34, respectively.

Comparison between the Comparative Examples 11 and 12 and Examples 5 and 6 shows that in view of the prior mixing of phosphite or phosphonite and acid-binding metal salt treated with the surface conditioning agent prior to mixing or compounding with the styrenic resin, the hydrolysis problem can be eliminated.

The description described above only illustrates the preferred embodiments, and it is not intended to limit this invention to these embodiments. It is apparent that various modifications and variations not departing from the spirit of the present invention are included within the scope of this invention.

We claim:

1. A process for producing a styrenic resin composition comprising the steps of:

compounding 100 parts by weight of a styrenic resin having a water content greater than 2% by weight, and 0.01–5.0 parts by weight of an organic phosphorus-containing antioxidant in an extruder to form said styrenic resin composition;

wherein said phosphorous-containing antioxidant is formed by mixing (a) 20 to 99.9 wt % of organic phosphite or phosphonite with (b) 0.1 to 80 wt % of acid-binding metal salt treated with a surface conditioning agent, prior to mixing or compounding with said styrenic resin;

wherein the weight ratio of said surface conditioning agent to said acid-binding metal salt is 0.1 to 50 wt %:99.9 to 50 wt %;

wherein said surface conditioning agent is selected from the group consisting of silane coupling agents, titanate coupling agents, zirconate coupling agents, aluminate coupling agents, zirco-aluminate coupling agents, non-ionic surfactants, and anionic surfactants;

wherein said styrenic resin having a water content greater than 2% by weight comprises 5–100 wt % of a rubbery graft copolymer (A) and 95–0 wt % of a styrenic copolymer (B) based on the dry weight of said styrenic resin;

wherein said rubbery graft copolymer(A) is prepared by graft polymerization of 50–90 wt % of styrenic monomer, 10–50 wt % of vinyl cyanide monomer, and 0–40 wt % of copolymerizable monomer in the presence of a rubbery polymer latex, followed by coagulation and recovery to have a water content of 5–50 wt %; and wherein said styrenic copolymer(B) is prepared by copolymerization of 50–90 wt % of styrenic monomer, 10–50 wt % of vinyl cyanide monomer, and 0–40 wt % of copolymerizable monomer.

2. The process of claim 1, wherein said surface conditioning agent is silane coupling agent.

3. The process of claim 1, wherein said acid-binding metal salt is hydrotalcite.

4. The process of claim 1, wherein said acid-binding metal salt is zeolite.

5. The process of claim 1, wherein said acid-binding metal salt is A type zeolite.

6. The process of claim 1, wherein the water content of said styrenic resin is greater than 5% by weight.

7. The process of claim 1, wherein said phosphorous-containing antioxidant is made by mixing said organic phosphite or phosphonite, said acid-binding metal salt treated with a surface conditioning agent, and a carrier, said carrier being an organic compound and having a melting point higher than that of said phosphorous-containing antioxidant.

8. The process of claim 7, wherein said phosphorous-containing antioxidant contains 25 to 150 parts by weight of said carrier per 100 parts of (a) organic phosphite or phosphonite and (b) acid-binding metal salt treated with a surface conditioning agent.

* * * * *